(12) United States Patent
Lecuivre

(10) Patent No.: US 9,598,801 B2
(45) Date of Patent: Mar. 21, 2017

(54) KNIT WITH STRIPS WITHOUT BARBS, METHOD OF MAKING SAME AND PROSTHESES MADE FROM SAID KNIT

(71) Applicant: Sofradim Production, Trévoux (FR)

(72) Inventor: Julie Lecuivre, Jassans-Riottier (FR)

(73) Assignee: Sofradim Production, Trevoux (FR)

( * ) Notice: Subject to any disclaimer, the term of this patent is extended or adjusted under 35 U.S.C. 154(b) by 254 days.

(21) Appl. No.: 14/366,349

(22) PCT Filed: Dec. 27, 2012

(86) PCT No.: PCT/EP2012/076977
§ 371 (c)(1),
(2) Date: Jun. 18, 2014

(87) PCT Pub. No.: WO2013/098343
PCT Pub. Date: Jul. 4, 2013

(65) Prior Publication Data
US 2014/0364684 A1 Dec. 11, 2014

(30) Foreign Application Priority Data
Dec. 29, 2011 (FR) ...................................... 11 62528

(51) Int. Cl.
*D04B 21/12* (2006.01)
*A61L 27/26* (2006.01)
(Continued)

(52) U.S. Cl.
CPC ............ *D04B 21/12* (2013.01); *A61F 2/0036* (2013.01); *A61F 2/0063* (2013.01); *A61L 27/26* (2013.01);
(Continued)

(58) Field of Classification Search
CPC .......................................... D04B 21/02–21/12
See application file for complete search history.

(56) References Cited

U.S. PATENT DOCUMENTS 4,931,343 A * 6/1990 Becker ............... A44B 18/0003
156/72
5,503,892 A * 4/1996 Callaway ............... D04B 21/04
15/209.1
(Continued)

FOREIGN PATENT DOCUMENTS

CN 2128637 Y 3/1993
CN 101842049 A 9/2010
(Continued)

OTHER PUBLICATIONS

International Search Report for PCT/EP12/076977 date of completion is Apr. 18, 2013 (2 pages).
(Continued)

*Primary Examiner* — Danny Worrell

(57) ABSTRACT

The present invention relates to an openwork prosthetic knit (1) made from a single piece based on at least a first yarn made of biocompatible polymer material that defines a first face (2) and a second face that are opposite one another and from a second biocompatible yarn that generates barbs (5) that protrude outwards from at least said first face, characterized in that said first face comprises at least one longitudinal strip (4) in the direction of the manufacture of said knit, over which it is provided with said barbs (5), and at least one longitudinal strip (3) in the direction of the manufacture of said knit, over which it is free of such barbs. It also relates to a process for manufacturing such a knit (1) and to a prosthesis comprising such a knit (1).

10 Claims, 1 Drawing Sheet

(51) Int. Cl.
*D04B 21/04* (2006.01)
*D04B 35/34* (2006.01)
*A61F 2/00* (2006.01)

(52) U.S. Cl.
CPC ............ *D04B 21/04* (2013.01); *D04B 35/34* (2013.01); *A61F 2/0045* (2013.01); *A61F 2002/0068* (2013.01); *A61F 2220/0016* (2013.01); *A61F 2240/001* (2013.01); *A61L 2400/18* (2013.01); *D10B 2501/0632* (2013.01); *D10B 2509/08* (2013.01)

(56) References Cited

U.S. PATENT DOCUMENTS

| | | | | |
|---|---|---|---|---|
| 6,843,077 | B1* | 1/2005 | Ishihara | A44B 18/0023 66/194 |
| 6,910,353 | B2* | 6/2005 | Sasser | A44B 18/0034 24/445 |
| 6,988,386 | B1* | 1/2006 | Okawa | A44B 18/0023 66/195 |
| 7,207,195 | B2* | 4/2007 | Okawa | A44B 18/0023 66/193 |
| 7,231,789 | B2* | 6/2007 | Chou | A44B 18/0023 66/191 |
| 7,325,421 | B2* | 2/2008 | Sasser | A44B 18/0034 66/195 |
| 7,331,199 | B2* | 2/2008 | Ory | A61F 2/0063 66/170 |
| 2004/0022993 | A1* | 2/2004 | Wildeman | A44B 18/0011 428/92 |
| 2004/0054376 | A1 | 3/2004 | Ory et al. | |

FOREIGN PATENT DOCUMENTS

| | | |
|---|---|---|
| CN | 101883538 A | 11/2010 |
| DE | 102009015302 A1 | 9/2010 |
| EP | 2 229 918 A1 | 9/2010 |
| FR | 2 924 330 A1 | 6/2009 |
| WO | WO 01/81667 A1 | 11/2001 |
| WO | 2010029438 A1 | 3/2010 |

OTHER PUBLICATIONS

Chinese Office Action dated Apr. 17, 2015 in corresponding Chinese Patent Application No. 201280065605.8, together with English translation, 17 pages.
Chinese Office Action dated Dec. 31, 2015 in corresponding Chinese Patent Application No. 201280065605.8, together with English translation, 19 pages.
Chinese Office Action (with English Translation), issued Apr. 17, 2015, corresponding to Chinese Patent Application No. 201280065222.0; 21 pages.
Australian Examination Report issued Aug. 8, 2016 in corresponding Australian Patent Application No. 2012360851, 3 pages.

* cited by examiner

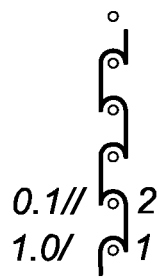 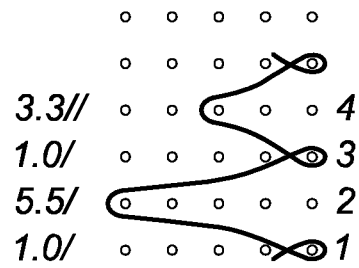 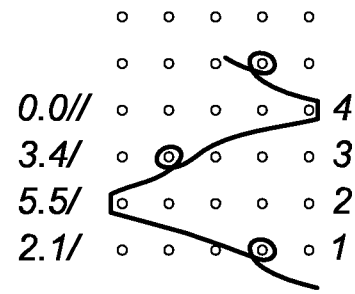
*Fig. 1A*    *Fig. 1B*    *Fig. 1C*
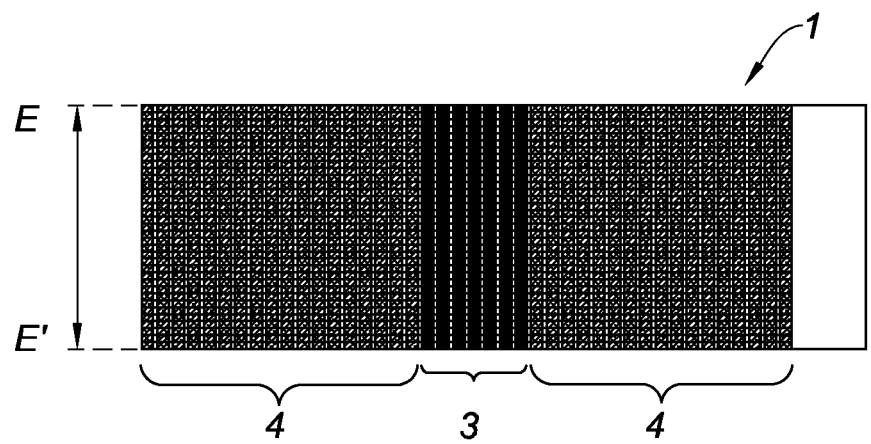
*Fig. 2*
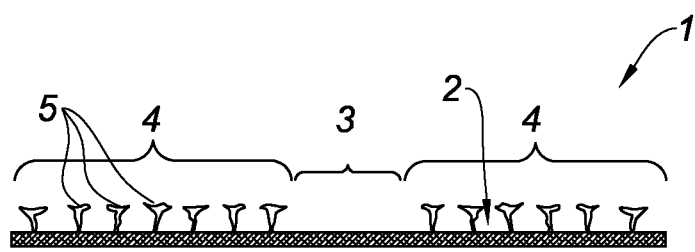
*Fig. 3*

KNIT WITH STRIPS WITHOUT BARBS, METHOD OF MAKING SAME AND PROSTHESES MADE FROM SAID KNIT

CROSS-REFERENCE TO RELATED APPLICATIONS

This application is a National Stage Application of PCT/EP12/076977 under 35 U.S.C. §371 (a), which claims priority of French Patent Application Serial No. 11/62528 filed Dec. 29, 2011, the disclosures of each of the above-identified applications are hereby incorporated by reference in their entirety.

The present invention relates to a prosthetic knit made from a single piece, at least one face of which comprises one or more strips provided with barbs and one or more strips free of barbs. Such a knit can particularly be used for producing prostheses requiring variable fastening capabilities, for example for fastening to biological tissues, on the surface of said prosthesis.

Wall reinforcement prostheses, for example for the abdominal wall, are widely used in surgery. These prostheses are intended to treat hernias by temporarily or permanently filling a tissue defect. These prostheses are generally made of biocompatible prosthetic fabric and can have a number of shapes, for example rectangular, circular or oval, depending on the anatomical structure to which they are to be fitted. Some of these prostheses are made from entirely bioresorbable yarns and are intended to disappear after having performed their reinforcing role while cell colonization takes place and tissue rehabilitation takes over. Others comprise non-bioresorbable yarns and are intended to remain permanently in the body of the patient.

Some of these prostheses are made from an arrangement of yarns, a knit, a woven or non-woven fabric, comprising barbs protruding outwards from one face of the prosthesis: these barbs constitute hooks that are able to fix themselves either in another prosthetic fabric, belonging to the same prosthesis or not, or directly in the biological tissues, for example the abdominal wall.

The presence of barbs capable of fastening directly to biological tissues makes it possible to do away with additional means of attachment for the prosthesis, such as staples, sutures, etc. However, in certain cases, for example when the prosthesis must be implanted in the vicinity of fragile or sensitive organs, such as vessels, nerves, or else the spermatic cord, it may prove advantageous for the part of the prosthesis in contact with these organs to be free of such barbs.

In such cases, a composite prosthesis is generally produced comprising a first textile portion with barbs and a second textile portion without barbs that is assembled to the first portion, for example by means of stitching, or ultrasonic welding, etc. Such a process is tedious and complicated. Furthermore, due to the discontinuous nature of the textile making up the composite prosthesis thus obtained, the mechanical properties of the prosthesis are not the same over the whole of the prosthesis. In particular, the assembly zone of the first textile portion to the second textile portion generally constitutes a line of weakness of the prosthesis.

Therefore, there remains a need for a knit that makes it possible to provide a reinforcing prosthesis both with zones that have good fastening capabilities and smoother and non-traumatizing zones, and which would not require additional steps during its manufacturing process.

The present invention aims to meet this need by proposing a knit made of a single piece, at least one face of which has one or more longitudinal strips provided with barbs and one or more longitudinal strips free of such barbs.

The present invention relates to an openwork prosthetic knit made from a single piece based on at least a first yarn made of biocompatible polymer material that defines a first face and a second face that are opposite one another and from a second biocompatible yarn that generates barbs that protrude outwards from at least said first face, characterized in that said first face comprises at least one longitudinal strip in the direction of the manufacture of said knit, over which it is provided with said barbs, and at least one longitudinal strip in the direction of the manufacture of said knit, over which it is free of such barbs.

The present invention also relates to a process for manufacturing a knit such as above comprising the following steps:

a) manufacture of an arrangement of first yarns of biocompatible polymer materials that define a first face and a second face that are opposite one another for said knit and of at least one second yarn, biocompatible heat-fusible monofilament yarn, that forms small loops that protrude outwards from said first face, by knitting on a warp or Raschel knitting machine, of said first yarns and of said second yarn using at least three guide bars, said first yarns being threaded, continuously on two of said three guide bars, over the whole of the width of said knitting machine, said second yarn being threaded, intermittently on the third guide bar, only over a width corresponding to the width of the strip(s) provided with barbs of said knit, b) cutting, by melting, of said loops, each loop generating two barbs.

Step b) of melting the loops of the above process is described for example in document WO01/81667.

In the present application, the expression "prosthetic knit" is understood to mean a knit intended to be implanted in the human or animal body in the form of a prosthesis or of any other part made at least partly with said knit.

In the present application, the expression "openwork knit" is understood to mean a knit having a weave or weaves that determine cells or voids in the thickness of the knit and on the faces of the knit, these cells or voids possibly forming channels that open on both sides of the knit. Such an openwork knit enables better tissue integration.

The expression "knit made from a single piece" is understood according to the present application to mean that the knit is produced in a single knitting step and does not comprise additional textile added by any means of attachment such as stitching, ultrasonic welding, etc. Thus, the knit according to the invention has mechanical properties that are constant over the whole of its surface, independently of the presence or absence of barbs on the longitudinal strips.

The first yarns of the knit according to the invention may be monofilament and/or multifilament yarns, and may be made from any biodegradable or non-biodegradable biocompatible material. Thus, the biodegradable materials suitable for the first yarns of the knit of the present invention may be selected from polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), copolymers thereof and mixtures thereof. The non-biodegradable materials suitable for the first yarns of the knit of the present invention may be selected from polyethylene terephthalate (PET), polyamides, aramids, expanded polytetrafluoroethylene, polyurethane, polyvinylidene difluoride (PVDF), butyl ester polymers, polyetheretherketone (PEEK), polyolefins (such as polyethylene or polypropylene), polyethers, copper alloys, silver or platinum alloys, medical grades of steel such as medical-grade stainless steel, and combinations thereof.

In one embodiment of the invention, said first face comprises several of said longitudinal strips provided with barbs that protrude outwards, and several of said longitudinal strips which are free of such barbs.

In the longitudinal strip(s) where they are present, the barbs of the knit according to the invention may protrude from the first face substantially perpendicular to the plane of said face or alternatively along one or more planes that are inclined relative to the plane of said face. Generally, these barbs have the shape of a shaft, having the diameter of the yarn used for their formation, surmounted by a head having a diameter greater than that of the shaft.

For example, the first face of the knit according to the invention may comprise several longitudinal strips free of barbs, these strips being intended to be located opposite fragile or sensitive organs once the prosthesis or knit is implanted, the remainder of the first face of the knit being provided with barbs located opposite other organs, for example muscles, to which they will be able to fasten in order to attach the knit or the prosthesis.

Alternatively, these barbs may be intended to be entangled in one or more arrangements of yarns, fibres, filaments and/or multifilaments of another prosthetic textile, for example in order to form a composite reinforcing prosthesis, in particular if it is desired, for example, for only certain strips of the knit according to the invention to fasten in this other prosthetic textile.

Thus, it is possible to prepare knits having a central longitudinal strip free of barbs, and two lateral longitudinal strips provided with barbs. It is for example possible to cut out transversely in such a knit prostheses for the manufacture of bands for treating urinary incontinence in women, such bands having a relatively smooth and atraumatic central portion for placing opposite the urethra, and corresponding to the central longitudinal strip of the knit during the manufacture thereof before cutting, and two outermost portions with barbs for attachment to the surrounding tissues, these two outermost portions of the prosthesis corresponding to the two lateral longitudinal strips of the knit during the manufacture thereof before cutting.

In one embodiment, the second yarn is a heat-fusible monofilament yarn. Thus, the step of manufacturing the barbs is facilitated, as will become apparent from the description that follows. In particular, in one embodiment, said barbs protrude outwards from said first face over a length ranging from 1 to 2 mm, preferably over a length of around 1.5 mm. Such a length of the barbs enables both a good fastening of the barbs to the biological tissues and an optimized manufacturing process. Such a length of the barbs makes it possible in particular to preserve the integrity of the yarns forming the knit during the formation of the barbs by melting of the loops as described in WO01/81667.

In one embodiment of the invention, said second yarn is a monofilament yarn made of polylactic acid.

In one embodiment of the invention, the width of the longitudinal strip(s) free of barbs varies from 1 cm to 3 cm. Such embodiments allow a facilitated and optimized manufacturing process. Such a small width makes it possible in particular to preserve the integrity of the yarns forming the knit during the step of melting the loops in order to obtain the barbs as described in WO01/81667.

In one embodiment of the invention, the chart followed for the knitting of said first and second yarns is selected from the following charts:

for said first yarns, threaded on two guide bars B1 and B2, according to the ISO 11676 standard:
  bar B1: 1.0/0.1//
  bar B2: 1.0/5.5/1.0/3.3// or 1.0/7.7/6.6/7.7// for said second yarn, threaded on the third guide bar B3, according to the ISO 11676 standard:
  bar B3: 2.1/5.5/3.4/0.0//

In embodiments, the first yarns are made of polyethylene terephthalate, and the second yarn is made of of polylactic acid.

For example, the second yarn may be threaded intermittently according to the following threading plan: (1 full-3 empty)×60, 1 full, 19 empty, (1 full-3 empty)×60. Alternatively, the second yarn may be threaded intermittently according to the following threading plan: (1 full-3 empty)×60, 1 full, 15 empty, (1 full-3 empty)×60. Alternatively, the second yarn may be threaded intermittently according to the following threading plan: (1 full-3 empty)×60, 1 full, 11 empty, (1 full-3 empty)×60.

The advantages of the present invention will emerge from the following examples and from the figures in which:

FIGS. 1A to 1C show the respective charts of three guide bars used for obtaining a knit according to the invention, FIG. 2 is a partial top view of a knit according to the invention, FIG. 3 is a cross section of the knit from FIG. 2.

EXAMPLES

Example 1

The following knit according to the invention is produced on a warp knitting machine:

Knit A: having the following chart according to the ISO 11676 standard:
  bar B1: 1.0/0.1//
  bar B2: 1.0/5.5/1.0/3.3//
  bar B3: 2.1/5.5/3.4/0.0//

The respective charts for bars B1, B2 and B3 are illustrated in FIGS. 1A to 1C.

Alternatively, the chart of bar B2 could be replaced by the following: 1.0/7.7/6.6/7.7//

Bar B1 and bar B2 are each threaded continuously 1 full, 1 empty, over the width of the knitting machine with a monofilament yarn made of polyethylene terephthalate (PET) having a diameter of 0.08 mm, commercially available from the company SIDER ARC.

Bar B3, which will give rise to the barbs, is threaded intermittently with a heat-fusible monofilament yarn made of polylactic acid having a diameter of 0.15 mm, according to the following threading plan:

(1 full-3 empty)×60, 1 full, 19 empty, (1 full-3 empty)×60

The knitting according to the chart above leads to the formation of loops that protrude outwards from one face of the knit by the heat-fusible monofilament made of polylactic acid.

The knit 1 obtained, after cutting the loops by melting as described in WO01/81667 in order to obtain barbs, is shown in FIGS. 2 and 3: the first face, namely the top face 2 in FIGS. 2 and 3, has a central longitudinal strip 3 in the direction EE' of the manufacture of said knit 1, on which it is free of barbs and two lateral strips 4 provided with barbs 5. Generally the barbs 5 have the shape of a shaft having the diameter of the yarn used for their formation, surmounted by a head having a diameter greater than that of the shaft. The barbs 5 protrude outwards from the first face 2 over a length of around 1.5 mm. Such a length of the barbs 5 enables a good fastening of the barbs in the biological tissues during the implantation of the knit 1 or of a prosthesis comprising this knit 1. Furthermore, such a length of the barbs 5 makes it possible in particular to preserve the integrity of the monofilament yarns made of polyethylene terephthalate (PET) forming the knit 1 during the formation of the barbs by melting the loops as described in WO01/81667, the hotplate used for melting the loops thus being kept at a sufficient distance from the monofilament yarns made of polyethylene terephthalate (PET) that form the ground structure of the knit 1.

The central longitudinal strip 3 has a width of around 1.8 cm. Such a small width makes it possible to preserve the integrity of the monofilament yarns made of polyethylene terephthalate (PET) forming the ground structure of the knit 1 during the step of melting the loops in order to obtain the barbs 5.

Thus, the heat-fusible monofilament yarn is threaded on the bar B3, only over a width corresponding to the sum of the widths of the two lateral strips 4 provided with barbs 5 of said knit 1.

Such a knit 1 has the same mechanical properties as the knit which would be obtained if the heat-fusible monofilament yarn was threaded continuously 1 full, 3 empty, on the bar B3 over the total width of the knitting machine.

Example 2

A knit is produced with the same yarns and charts as those from EXAMPLE 1, the knit according to the present example differing from that of EXAMPLE 1 only by the threading of the bar B3, this threading being:

(1 full-3 empty)×60, 1 full, 15 empty, (1 full-3 empty)×60

The knit obtained, after cutting the loops by melting as described in WO01/81667 in order to obtain barbs, is similar to that from FIGS. 2 and 3, but with a narrower central strip. In the present example, the first face of the knit has a central longitudinal strip in the direction of the manufacture of said knit, on which it is free of barbs, having a width of around 1.4 cm. Such a small width makes it possible to preserve the integrity of the monofilament yarns made of polyethylene terephthalate (PET) that form the ground structure of the knit during the step of melting the loops in order to obtain the barbs.

Such a knit has the same mechanical properties as the knit which would be obtained if the heat-fusible monofilament yarn was threaded continuously 1 full, 3 empty, on the bar B3 over the total width of the knitting machine.

Example 3

A knit is produced with the same yarns and charts as those from EXAMPLE 1, the knit according to the present example differing from that of EXAMPLE 1 only by the threading of the bar B3, this threading being:

(1 full-3 empty)×60, 1 full, 11 empty, (1 full-3 empty)×60

The knit obtained, after cutting the loops by melting as described in WO01/81667 in order to obtain barbs, is similar to that from EXAMPLE 2, but with an even narrower central strip. In the present example, the first face of the knit has a central longitudinal strip in the direction of the manufacture of said knit, on which it is free of barbs, having a width of around 1 cm. Such a small width makes it possible to preserve the integrity of the monofilament yarns made of polyethylene terephthalate (PET) that form the ground structure of the knit during the step of melting the loops in order to obtain the barbs.

Such a knit has the same mechanical properties as the knit which would be obtained if the heat-fusible monofilament yarn was threaded continuously 1 full, 3 empty, on the bar B3 over the total width of the knitting machine.

The knits from Examples 1 to 3 above may be used as they are or in combination with other textiles in order to form reinforcing prostheses, for example abdominal wall reinforcing prostheses, or else bands for treating urinary incontinence.

The invention claimed is:

1. A process for manufacturing a knit, comprising the following steps:
   a) manufacturing an arrangement of first and second yarns, said first yarn comprising a biocompatible polymer material that define a first face and a second face that are opposite one another and said second yarn comprising a biocompatible heat-fusible monofilament yarn, that forms small loops that protrude outwards from said first face, by knitting on a warp or Raschel knitting machine, of said first yarns and of said second yarn using at least three guide bars, said first yarns being threaded, continuously on two of said three guide bars, over a whole of a width of said knitting machine, said second yarn being threaded, intermittently on the third guide bar, only over a width corresponding to the width of the first longitudinal strip provided with barbs of said knit, wherein the knitting of said first and second yarns is according to the following charts:
   for said first yarns, threaded on two guide bars B1 and B2, according to the ISO 11676 standard:
   bar B1: 1.0/0.1//
   bar B2: 1.0/5.5/1.0/3.3// or 1.0/7.7/6.6/7.7//
   for said second yarn, threaded on the third guide bar B3, according to the ISO 11676 standard:
   bar B3: 2.1/5.5/3.4/0.0//
   b) cutting, by melting, of said loops, each loop generating two barbs.

2. The process according to claim 1, wherein the first yarns are made of polyethylene terephthalate, and the second yarn is made of polylactic acid.

3. The process according to claim 1, wherein the second yarn is threaded intermittently according to the following threading plan: (1 full-3 empty)×60, 1 full, 19 empty, (1 full-3 empty)×60.

4. The process according to claim 1, wherein the second yarn is threaded intermittently according to the following threading plan:
   (1 full-3 empty)×60, 1 full, 15 empty, (1 full-3 empty)×60.

5. The process according to claim 1, wherein the second yarn is threaded intermittently according to the following threading plan:
   (1 full-3 empty)×60, 1 full, 11 empty, (1 full-3 empty)×60.

6. The process according to claim 1, wherein the knit further comprises first zones that have fastening capabilities and second zones that are smooth and non-traumatizing.

7. A prosthetic implant for tissue reinforcement comprising at least one knit manufactured according to claim 1.

8. A process for manufacturing a knit, comprising the following steps:
   a) manufacturing an arrangement of first and second yarns, said first yarn comprising a biocompatible polymer material that define a first face and a second face that are opposite one another and said second yarn comprising a biocompatible heat-fusible monofilament yarn, that forms small loops that protrude outwards from said first face, by knitting on a warp or Raschel knitting machine, of said first yarns and of said second yarn using at least three guide bars, said first yarns being threaded, continuously on two of said three guide bars, over a whole of a width of said knitting machine, said second yarn being threaded, intermittently on the third guide bar, only over a width corresponding to the width of the first longitudinal strip provided with barbs of said knit, wherein the second yarn is threaded intermittently according to the following threading plan:

(1 full-3 empty)×60, 1 full, 19 empty, (1 full-3 empty)×60 b) cutting, by melting, of said loops, each loop generating two barbs.

9. A process for manufacturing a knit, comprising the following steps:

a) manufacturing an arrangement of first and second yarns, said first yarn comprising a biocompatible polymer material that define a first face and a second face that are opposite one another and said second yarn comprising a biocompatible heat-fusible monofilament yarn, that forms small loops that protrude outwards from said first face, by knitting on a warp or Raschel knitting machine, of said first yarns and of said second yarn using at least three guide bars, said first yarns being threaded, continuously on two of said three guide bars, over a whole of a width of said knitting machine, said second yarn being threaded, intermittently on the third guide bar, only over a width corresponding to the width of the first longitudinal strip provided with barbs of said knit, wherein the second yarn is threaded intermittently according to the following threading plan:

(1 full-3 empty)×60, 1 full, 15 empty, (1 full-3 empty)×60 b) cutting, by melting, of said loops, each loop generating two barbs.

10. A process for manufacturing a knit, comprising the following steps:

a) manufacturing an arrangement of first and second yarns, said first yarn comprising a biocompatible polymer material that define a first face and a second face that are opposite one another and said second yarn comprising a biocompatible heat-fusible monofilament yarn, that forms small loops that protrude outwards from said first face, by knitting on a warp or Raschel knitting machine, of said first yarns and of said second yarn using at least three guide bars, said first yarns being threaded, continuously on two of said three guide bars, over a whole of a width of said knitting machine, said second yarn being threaded, intermittently on the third guide bar, only over a width corresponding to the width of the first longitudinal strip provided with barbs of said knit, wherein the second yarn is threaded intermittently according to the following threading plan:

(1 full-3 empty)×60, 1 full, 11 empty, (1 full-3 empty)×60 b) cutting, by melting, of said loops, each loop generating two barbs.

* * * * *